(12) United States Patent
Ogi et al.

(10) Patent No.: US 6,187,324 B1
(45) Date of Patent: Feb. 13, 2001

(54) COSMETIC COMPOSITION COMPRISING AT LEAST ONE OF KUMAZASA EXTRACT AND MEDICINAL CARBON

(75) Inventors: Takehiko Ogi, Shiga; Tadahiko Takei, Nagano, both of (JP)

(73) Assignee: Kabushiki Kaisha Ogi Kogei, Shiga (JP)

( * ) Notice: Under 35 U.S.C. 154(b), the term of this patent shall be extended for 0 days.

(21) Appl. No.: 09/337,071

(22) Filed: Jun. 21, 1999

Related U.S. Application Data

(63) Continuation-in-part of application No. 09/301,401, filed on Apr. 28, 1999.

(30) Foreign Application Priority Data

Aug. 11, 1998 (JP) .................................. 10-226712

(51) Int. Cl.⁷ .............................. A61K 6/00; A01N 65/00
(52) U.S. Cl. ........................ 424/401; 424/69; 424/195.1; 424/78.05
(58) Field of Search .................... 424/401, 69, 195.1, 424/78.05

(56) References Cited

U.S. PATENT DOCUMENTS

| 4,481,205 | * | 11/1984 | Von Bebenburg et al. | 424/263 |
| 5,494,667 | * | 2/1996 | Uchida et al. | 424/195.1 |
| 5,780,020 | * | 7/1998 | Peterson et al. | 424/65 |

OTHER PUBLICATIONS

Japan 62211068 Abstract, Mar. 1986.*
Japan 04082558 Abstract, Jul. 1990.*
Inamo Mark, "Airfresheners & Deodorizers: Biofilter: BF1" Comline–Consumer Goods, Abstract, Aug. 1997.*
Miyano, et al. EP 376448—Eur. Pat Appl. Abstract, Nov. 1989.*
Iwamoto, et al. JP 10328283—Abstract Jpn. Kokai Tokkyo Koho, Dec. 1998.*

* cited by examiner

Primary Examiner—Thurman K. Page
Assistant Examiner—Isis Ghali
(74) Attorney, Agent, or Firm—Jordan and Hamburg LLP

(57) ABSTRACT

A cosmetic composition comprising at least one of Kumazasa extract and medicinal carbon. The cosmetic composition exhibits an excellent deodorizing effect and antibacterial effect, and is applied to toilet soap, facial cleansing cream, shampoo, rinse, etc.

8 Claims, No Drawings

COSMETIC COMPOSITION COMPRISING AT LEAST ONE OF KUMAZASA EXTRACT AND MEDICINAL CARBON

This is a continuation-in-part of prior application Ser. No. 09/301,401.

BACKGROUND OF THE INVENTION

1. Field of the Invention

The present invention relates to cosmetic compositions for toilet soap, facial cleansing cream, shampoo, rinse, and the like.

2. Discussion of the Background

A variety of cosmetic compositions are used for toilet soap, facial cleansing cream, shampoo, rinse, etc. Recently, there have been developed cosmetic compositions that produce an antibacterial effect or a deodorizing effect.

However, those conventional cosmetic compositions include synthetic compounds, which may pose a safety problem against the human body. Some cosmetic compositions exhibit an insufficient antibacterial effect or deodorizing effect.

It is an object of the invention to provide a cosmetic composition which is capable of exhibiting excellent antibacterial effect and deodorizing effect, while avoiding harmful effects against the human body.

To achieve the above object, there has been provided a cosmetic composition which contains at least one of Kumazasa extract and charcoal. Kumazasa is a plant of the species Sasa albo-marginata. Kumazasa extract is extracted from leaves of Kumazasa by using an ethanol solution, or prepared by other conventional methods. The charcoal is preferably activated charcoal, which is called medicinal carbon in the Pharmacopoeia Japonica. It is known that Kumazasa mainly contains polysaccharides, chlorophyll, vitamin $B_1$, vitamin $B_2$, organic acids, β-amyrin, minerals, amino acids, etc.

Kumazasa extract exhibits an excellent bactericidal effect and antiinflammatory effect. It is presumable that the bactericidal effect of Kumazasa is obtainable since chlorophyllin, which is a derivative obtained by subjecting chlorophyll of Kumazasa to alkali hydrolysis, exhibits the bactericidal properties, acting directly over some types of bacteria, particularly anaerobic bacteria. Kumazasa also exhibits an adsorption effect and a deodorization effect.

On the other hand, charcoal is a porous material, and therefore exhibits the adsorption effect, thereby exhibiting the deodorization effect.

DETAILED DESCRIPTION OF THE PREFERRED EMBODIMENT

Embodiments of the present invention will be described hereinbelow.

Embodiment 1

A Kumazasa-containing cosmetic composition applied to a facial pack will be discussed in this embodiment. The components of the Kumazasa-containing cosmetic composition are as follows:

| Components | % by weight |
| --- | --- |
| Kumazasa extract | 1.5 |
| dipotassium glycylrhizin acid | 0.1 |
| hyaluronic acid | 1.0 |
| chlorophyll | 0.5 |
| thickener (Carboxyvinylpolymer) | 1.0 |
| Sodium Alginate | 0.5 |
| Monococonut fatty acid POE (20) sorbitan | 0.1 |
| neutralizer (TEA) | 1.0 |
| water | balance to 100% |

Of the components, dipotassium glycylrhizin acid is extracted from Licorice (sweet root), and exhibits a detoxication effect, an anti-allergic effect, an anti-peptic ulcer effect, an anti-dermatitis effect, etc. Hyaluronic acid exhibits an excellent moisture retention effect and an excellent permeability, thereby giving a supple appearance to the skin. Chlorophyll exhibits the deodorization effect. Sodium Alginate is prepared by purifying an extract of sea weed.

Embodiment 2

A Kumazasa-containing cosmetic composition applied to an external skin treatment agent will be discussed in this embodiment. The components of the Kumazasa-containing cosmetic composition are as follows:

| Components | % by weight |
| --- | --- |
| Kumazasa extract | 1.0 |
| emulsifier (S-308) | 3.0 |
| synthetic oil (C10) | 3.0 |
| Jojoba oil | 1.5 |
| emulsified dispersing agent (TL-10) | 2.0 |
| amide-amine | 2.0 |
| Behenyl | 1.5 |
| lipophilic type emulsifier (BO-308) | 1.0 |
| thickener (AM-301) | 4.0 |
| hydrolysis collagen peptide (CCP-100) | 0.5 |
| Scutellaria root extract | 0.1 |
| Rosemary extract | 0.1 |
| Aloe Vera extract | 0.5 |
| chlorophyll | 1.0 |
| water | balance to 100% |

Of the components, Jojoba oil is oil extracted from a seed of a shrub of the type that grows in the northern part of Mexico. It has been recognized that Jojoba oil is effective for preventing pimples and dandruff. Scutellaria root extract is of a liquefied form extracted from Abiate. It has been recognized that Scutellaria root exhibits an antiinflammatory effect, an anti-allergic effect and an antibacterial effect. Rosemary extract is recognized as being effective for improving the circulation of the blood and preventing the loss of hair and dandruff. Aloe Vera extract is effective for limiting the formation of melanin in an incised wound or abrasion of the skin.

Embodiment 3

A Kumazasa-containing cosmetic composition applied to skin lotion will be discussed in this embodiment. The components of the Kumazasa-containing cosmetic composition are as follows:

| Components | % by weight |
| --- | --- |
| Kumazasa extract | 1.0 |
| glutamate (PCA soda) | 0.5 |
| hyaluronic acid | 1.0 |
| glycerin | 3.0 |
| 1:3 BG | 2.0 |
| chlorophyll | 1.0 |
| water | balance to 100% |

Of the components, PCA soda is effective for giving a moisture retention force and elasticity to the skin. 1:3 BG is prepared by adding hydrogen to the product of the aldol condensation reaction of acetaldehyde.

Embodiment 4

A Kumazasa-containing cosmetic composition applied to skin cream will be discussed in this embodiment. The components of the Kumazasa containing cosmetic composition are as follows:

| Components | % by weight |
| --- | --- |
| Kumazasa extract | 1.5 |
| nonionic surfactant active agent | 1.0 |
| lipophilic type emulsifier (MGS-DEX) | 1.0 |
| emulsifier (GO-430) | 1.0 |
| stearic acid | 4.0 |
| paraffin | 1.0 |
| beeswax | 3.0 |
| Behenyl | 3.0 |
| liquid paraffin | 20.0 |
| chlorophyll | 1.0 |
| collagen | 0.5 |
| hyaluronic acid | 0.5 |
| placenta | 0.5 |
| dipotassium glycylrhizin acid | 0.1 |
| antiseptic agent (M-P) | 0.1 |
| water | balance to 100% |

Of the components, collagen is a fibrous protein that constitutes the skin, etc., of Mammalia. It has been recognized that collagen exhibits effects for retaining moisture and maintaining elasticity of the skin, and restoring a young state of the skin.

Placenta is of a liquid form extracted from bovine, porcine, or ovine placenta. It has been recognized that placenta is effective for limiting and removing liver spots, freckles, fine wrinkles and rough dry skins.

Embodiment 5

A Kumazasa-containing cosmetic composition applied to facial soap will be discussed in this embodiment. The components of the Kumazasa-containing cosmetic composition are as follows:

| Components | % by weight |
| --- | --- |
| Kumazasa extract | 1.5 |
| glutamate (PCA soda) | 0.5 |
| Aloe Vera extract | 0.5 |
| chlorophyll | 1.0 |
| dipotassium glycylrhizin acid | 0.1 |
| 1:3 BG | 1.0 |

| Components | % by weight |
| --- | --- |
| Pyrotel CPI-40 | 1.0 |
| Amitel LGS-5 | 0.5 |
| Amisoft LS-11 | 1.0 |
| Soypon SC (sodium cocoyl sarcosine) | 1.0 |
| Lauryl Mono Phosphate | 1.0 |
| Lauric Acid Diethanolamide | 1.0 |
| water | balance to 100% |

Of the components, Pyrotel CPI-40 and Amisoft LS-11 are respectively available from Associates of Cape Cod, Inc., Woods Hole, Mass., and Ajinomoto K.K.

Embodiment 6

A charcoal-containing cosmetic composition applied to facial soap will be discussed in this embodiment. The components of the charcoal-containing cosmetic composition are as follows:

| Components | % by weight |
| --- | --- |
| activated charcoal | 1.0 |
| Talc | 4.0 |
| Kaolin | 5.0 |
| Bentonite | 1.7 |
| dipotassium glycylrhizin acid | 0.1 |
| Aloe Vera extract | 3.0 |
| vitamin C | 0.1 |
| hyaluronic acid | 1.0 |
| black iron oxide | 3.0 |
| emulsified dispersing agent (TL-10) | 1.0 |
| antiseptic agent (M-P) | 0.2 |
| 1:3 BG | 2.0 |
| water | balance to 100% |

Of the components, vitamin C is effective for limiting and removing an abnormal pigmentation of the skin.

Embodiment 7

A charcoal-containing cosmetic composition applied to shampoo will be discussed in this embodiment. The components of the charcoal-containing cosmetic composition are as follows:

| Components | % by weight |
| --- | --- |
| activated charcoal | 1.0 |
| amino acid | 3.5 |
| amisole | 1.0 |
| Pyrotel CPI-60 | 2.0 |
| Amitel LGO | 0.5 |
| emulsified dispersing agent (TL-10) | 5.0 |
| glycerin | 5.0 |
| antiseptic agent (P-P) | 0.1 |
| nonionic surfactant active agent (Twin-20) | 5.0 |
| black iron oxide | 3.0 |
| antiseptic agent (M-P) | 0.1 |
| chitin | 1.0 |
| Kumazasa extract | 0.5 |
| water | balance to 100% |

Of the components, chitin is extracted from Crustacea such as crabs and lobsters, and becomes effective for retaining moisture in the skin and the hair after sticking thereto.

Embodiment 8

A charcoal-containing cosmetic composition applied to solid toilet soap will be discussed in this embodiment. The components of the charcoal containing cosmetic composition are as follows:

| Components | % by weight |
|---|---|
| activated charcoal | 1.0 |
| beef tallow | 25.48 |
| coconut oil | 11.0 |
| hardened oil | 3.0 |
| ethanol | 25.0 |
| caustic soda | 19.0 |
| white sugar | 12.0 |
| water | 3.52 |

Other Embodiments

It is possible to include the powder of tourmaline, catechines, etc., in the cosmetic composition in each of the above embodiments. Tourmaline is generally called denki ishi in Japan. This has a crystalline structure of a hexagonal system having a hardness of 7.25 and a specific gravity of 3.05. Tourmaline is a polar crystal and therefore displays the property that electric polarization will occur even in the case that tourmaline is not placed in an electric field, unlike common derivatives. The composition of tourmaline is represented by the formula:

$$NaX_3Al_6(BO_3)_3Si_6O_{18}(OH)_4$$

in which X represents a metallic atom optionally selected from the group consisting Mg, Fe, Mn, Li and Al. Tourmaline is called Dravite (magnesia tourmaline) in the case that X represents Mg, schorl (iron tourmaline) in the case that X represents Fe or Mn, and Elbite (lithia tourmaline) in the case that X represents Li or Al. These various forms of tourmaline produce an excellent deodorizing effect via the adsorption effect caused by its electrostatic force.

On the other hand, catechines are contained in green tea, and exhibit an antioxidation effect.

In accordance with the present invention, the amount of Kumazasa extract in the cosmetic composition is preferably in the range of 0.1 to 10.0% by weight, more preferably 0.2 to 5.0% by weight, and most preferably 0.4 to 2.0% by weight. Further the suitable amount of charcoal in the cosmetic composition is preferably in the range of 0.05 to 2.0% by weight, more preferably 0.2 to 1.5% by weight and most preferably 0.5 to 1.0% by weight.

In the embodiments, the charcoal in the compositions is activated charcoal. However, it is also possible to use charcoals other than activated charcoal, such as charcoal of bamboo, Bincho charcoal (Japanese traditional charcoal, meaning a white coal of an ilex or a broadleaf tree), or charcoal of Hinoki (Japanese cypress).

When the cosmetic composition of the present invention contains Kumazasa extract, it exhibits an excellent antibacterial effect, as well as an excellent antiinflammatory effect via the bactericidal activity of Kumazasa.

Via the adsorption effects produced by Kumazasa or charcoal, it is possible to produce the deodorizing action.

In addition, since both Kumazasa and charcoal do not inherently produce a harmful effect against the human body, they are advantageous in view of the safety requirements for the human body as compared with the conventional cosmetic compositions including synthetic compounds.

When the cosmetic composition applied on the skin has been washed away, charcoal produces such an effect as to adsorb impurities in water.

Further, when cosmetic compositions according to the present invention contain both Kumazasa extract and charcoal, the components of the Kumazasa extract are adsorbed into the porous charcoal, so that the Kumazasa extract can produce the bactericidal activity for a prolonged period of time This specification is by no means intended to restrict the present invention to the preferred embodiments set forth therein. Various modifications to the cosmetic composition of the present invention, as described herein, may be made by those skilled in the art without departing from the spirit and scope of the present invention as defined in the appended claims.

What is claimed is:

1. A cosmetic composition comprising both Kumazasa extract and charcoal.

2. A cosmetic composition as set forth in claim 1, wherein said charcoal is activated charcoal.

3. A cosmetic composition as set forth in claim 1, wherein the amount of Kumazasa extract in the cosmetic composition is in the range of 0.1 to 10.0% by weight.

4. A cosmetic composition as set forth in claim 1, wherein the amount of Kumazasa extract in the cosmetic composition is in the range of 0.2 to 5.0% by weight.

5. The cosmetic composition as set forth in claim 1, wherein the amount of Kumazasa extract in the cosmetic composition is in the range of 0.4 to 2.0% by weight.

6. A cosmetic composition as set forth in claim 1, wherein the amount of charcoal in the cosmetic composition is in the range of 0.05 to 2.0% by weight.

7. A cosmetic composition as set forth in claim 1, wherein the amount of charcoal in the cosmetic composition is in the range of 0.2 to 1.5% by weight.

8. A cosmetic composition as set forth in claim 1, wherein the amount of charcoal in the cosmetic composition is in the range of 0.5 to 1.0% by weight.

* * * * *